US006428746B1

(12) United States Patent
Muscarella et al.

(10) Patent No.: US 6,428,746 B1
(45) Date of Patent: Aug. 6, 2002

(54) METHOD FOR DETERMINING THE EFFICACY OF A DECONTAMINATION PROCEDURE

(75) Inventors: Lawrence F. Muscarella, 501 Hancock Rd., North Wales, PA (US) 19454; Frank E. J. Weber, Doylestown, PA (US)

(73) Assignees: Custom Ultrasonics Inc., Buckingham; Lawrence F. Muscarella, N. Wales, both of PA (US)

( * ) Notice: Subject to any disclaimer, the term of this patent is extended or adjusted under 35 U.S.C. 154(b) by 0 days.

(21) Appl. No.: 09/497,487

(22) Filed: Feb. 4, 2000

(51) Int. Cl.[7] .............................. G05B 1/00; A01N 1/00
(52) U.S. Cl. ..................... 422/3; 422/1; 435/4; 435/29; 435/31
(58) Field of Search ............................ 422/1, 3; 435/4, 435/29, 31

(56) References Cited

U.S. PATENT DOCUMENTS 5,250,299 A * 10/1993 Good et al. ................ 424/94.4

OTHER PUBLICATIONS

Standard Test Method for Determination of Effectiveness of Sterilization Processes for Reusable Medical Devices, American Society for Testing and Materials, Designation: E 1766–95, pp. 1–4, Published Jan. 1986.

American Society For Testing and Materials, "*Standard Test Method to Determine Efficacy of Disinfection Processes for Reusable Medical Devices (Simulated Use Text)*[1]", no date, 5 pages.

* cited by examiner

*Primary Examiner*—Terrence R. Till
*Assistant Examiner*—Imad Soubra
(74) *Attorney, Agent, or Firm*—Blank Rome Comisky & McCauley LLP

(57) ABSTRACT

A method determines an efficacy of a decontamination procedure. The method includes providing a test object and a control object. The test object is contaminated with a first known amount of inoculum comprising microorganisms. The control object is contaminated with a second known amount of the inoculum. The first known amount of inoculum and the second known amount of inoculum are substantially the same. The decontamination procedure is performed on the contaminated test object but not on the contaminated control object. The microorganisms from the decontaminated test object and the contaminated control object are recovered. A number of microorganisms recovered from the decontaminated test object is compared with a number of microorganisms recovered from the contaminated control object. The decontamination procedure is deemed effective when the number of microorganisms recovered from the decontaminated test object is at least 3 logs less than the number of microorganisms recovered from the contaminated control object.

35 Claims, No Drawings

METHOD FOR DETERMINING THE EFFICACY OF A DECONTAMINATION PROCEDURE

FIELD OF THE INVENTION

This invention relates to methods for determining the efficacy of decontamination procedures, and more particularly, to a method for testing the efficacy of decontamination procedures for endoscopes and other lumened surgical instruments.

BACKGROUND OF THE INVENTION

Prior to placing any surgical instrument within a patient, the instrument should be decontaminated (i.e., cleaned, disinfected, sterilized and/or water-rinsed) to avoid infecting the patient with contaminants or microorganisms on the instrument. Decontamination is especially challenging for lumened instruments, such a flexible endoscopes, which are repeatedly contaminated and decontaminated. Endoscopes are particularly difficult to decontaminate due to their design, which includes a variety of internal channels that are difficult to clean and access.

Medical professionals have an ever-increasing variety of decontamination methods from which to select. Selecting an effective decontamination method would be easier if an evaluation method existed to determine the efficacy of different decontamination methods. Medical professionals could use such an evaluation method to verify and document that they adequately decontaminated their instruments prior to surgery.

Users and suppliers of decontamination equipment and accessories (e.g., detergents and sterilants) would also be aided by a method for determining the efficacy of different decontamination methods.

Surgical instrument manufacturers (e.g., flexible and rigid endoscope manufacturers) would also be aided by a method for determining the efficacy of different decontamination methods. These manufacturers potentially could show that their instruments can be effectively decontaminated, and could specify that the end user employ a specific decontamination method that has been verified as adequate (i.e., validated).

All references cited herein are incorporated herein by reference in their entireties.

SUMMARY OF THE INVENTION

A method determines the efficacy of a decontamination procedure. The method includes providing a test object and a control object. The test object is contaminated with a first known amount of inoculum that includes microorganisms. The control object is contaminated with a second known amount of the inoculum. The first known amount of inoculum and the second known amount of inoculum is substantially the same. The decontamination procedure is performed on the contaminated test object but not on the contaminated control object. The microorganisms from the decontaminated test object and the contaminated control object are recovered. A number of microorganisms recovered from the decontaminated test object is compared with a number of microorganisms recovered from the contaminated control object. The decontamination procedure is deemed effective when the number of microorganisms recovered from the decontaminated test object is at least 3 logs less than the number of microorganisms recovered from the contaminated control object.

Another embodiment of the method includes performing a first sampling technique on the decontaminated test object and a second sampling technique on the contaminated control object. The first sampling technique and the second sampling technique are the same and are operative to recover the microorganisms from respective ones of the decontaminated test object and the contaminated control object. The decontamination procedure is deemed effective relative to the sampling technique when the number of microorganisms recovered from the decontaminated test object is at least 3 logs less than the number of microorganisms recovered from the contaminated control object.

Conventional methods for evaluating the efficacy of a decontamination process that do not use control instruments can yield erroneous results. For example, a known amount of an inoculum of viable microorganisms is applied onto internal surfaces forming internal lumens of a test instrument. This instrument is decontaminated using a prescribed decontamination process. Typically, a sterile fluid is used for sampling the lumens. Usually, the sterile fluid is rinsed through one end of the lumen, collected aseptically at the opposite end of the lumen and then analyzed microbiologically.

The efficacy of the decontamination process is assessed by measuring and comparing the number of microorganisms recovered from fluid rinsed through the test instrument to the known number of microorganisms originally applied to the test instrument. The lower the number of recovered microorganisms, the more efficacious the process is presumed to be. If the fluid is found to be sterile, the lumen is assumed to be sterile due presumptively to the prescribed decontamination process having destroyed all of the microorganisms inoculated onto the lumen surfaces.

This conclusion might be erroneous, however. It cannot be assumed that because the rinsing fluid was sterile, the decontamination process must have destroyed all of the microorganisms. In order for this decontamination process to be valid, the sampling technique must recover every viable microorganism on the lumen surfaces after exposure to the decontamination process. The rinse sampling technique might be invalid because microorganisms that survive the decontamination process may adhere to the lumen surfaces and not be recovered during the rinse sampling technique. Thus, due to the limitations of the rinse sampling technique, the decontamination process may be presumed to have destroyed all of the microorganisms on the lumen surfaces when, in fact, some microorganisms may have survived but cannot be recovered by the sampling technique. The method uses a control object to remove this potential artifact from being introduced into the data.

DEFINITIONS

Bioburden: The number and type of viable microorganisms used to contaminate instruments.

CFU: Colony Forming Units.

CFU/ml: A concentration of microorganisms, expressed as colony forming units per unit milliliter of volume.

Cleaning: The removal of foreign materials, such as organic soil (e.g., protein and/or blood serum) and microorganisms, from an object such as, e.g., a medical instrument.

High-level Disinfection: The complete destruction and/or removal of all microbal life, except for high numbers of bacterial endoscopes.

Sterilization: The complete destruction and/or removal of all microorganisms.

Decontamination: The process of cleaning, disinfecting, sterilizing and/or water-rinsing an object. The object can be subjected to any combination or permutation of these steps.

Detergent solution: A solution used to aid in cleaning objects:

Automated decontamination: The use of an automated device to decontaminate objects.

Starting titre: The concentration of microorganisms (expressed as CFU/ml) used to contaminate both the control and test instruments.

Manual decontamination: The decontamination of objects without the aid of an automated device.

Accessible sites: Refers to those locations on a reusable medical instrument that can be accessed and decontaminated.

Inaccessible sites: Refers to those locations on a reusable medical instrument that cannot be accessed and decontaminated.

Worst-case conditions: The intentional exaggeration of one or more parameters to create a challenge unlikely to be encountered in the clinical setting.

Reusable medical instrument: Any medical instrument that is claimed by the manufacturer to be usable after being decontaminated.

Endoscope: A generic term for a medical instrument that is used to examine hollow viscera. Examples of flexible endoscopes include broncoscopes, gastroscopes and colonoscopes. Examples of rigid endoscopes include laparoscopes and arthroscopes. Flexible endoscopes typically include internal lumens, a complex valve system, and other surfaces that need to be decontaminated after each use.

Test cycle: Exposure of an instrument to at least one of the steps of the decontamination process (e.g., cleaning, disinfecting, sterilizing and/or rinsing).

Inoculum: A volume of the starting titre (CFU) of a type (genus and species) of viable microorganisms, and organic soil used to contaminate both the control and test instruments.

Control instruments: Reusable instruments that are contaminated but not subjected to the test cycle. These instruments are used to determine the number of organisms that can be recovered.

Test instruments: Reusable instruments that are contaminated and subjected to the test cycle. These instruments are used to determine the efficacy of the decontamination process.

Control instrument recovery: The number of viable microorganisms (CFU) recovered from the control instruments.

Test instrument recovery: The number of viable microorganisms (CFU) recovered from the test instruments.

Recovery count: The control instrument recovery. This number may be significantly less than the number in the applied inoculum. (If a high-level disinfection process is being evaluated, the recovery count must be equal to or greater than $1 \times 10^6$ CFUs of mycobacteria. This may require the starting titre to be as high as $1 \times 10^8$ CFU/ml.)

Recovery efficacy: A ratio, expressed as a percentage, of the recovery count to the applied inoculum. This value is multiplied by 100 to express efficacy as a percentage. Also, a measure, in part, of the effectiveness of the sampling method used to recover microorganisms.

Cleaning efficacy: The efficacy of cleaning may be calculated as a percentage or log reduction from the recovery count to the test instrument recovery. Typically, at least a 3 log reduction (99.9%) of bioburden is required.

Cleaning effectiveness: A measure of the effectiveness of the cleaning process and can be evaluated by comparing the number of microorganisms recovered from the test instruments to the recovery count. Cleaning effectiveness can be expressed as a percent or log reduction. Typically, at least a 3 log reduction (99.9%) of a marker microorganism is required to claim cleanliness.

Disinfection efficacy: The efficacy of disinfection may be calculated as a percent or log reduction from the recovery count to the test instrument recovery. Typically, at least a 6 log reduction (99.9999%) of mycobacterium is required.

Disinfection effectiveness: A measure of the effectiveness of the disinfection process and can be evaluated by comparing the number of microorganisms recovered. from the test instruments to be recovery count. Disinfection effectiveness can be expressed as a percent or log reduction. Typically, at least a 6 log reduction (99.9999%) of mycobacterium is required to claim high level disinfection.

Sterilization efficacy: The efficacy of a sporicidal process may be calculated as a percent or log reduction from the recovery count to the test instrument recovery. Typically, at least a 6 log reduction (99.9999%) of bacterial endospores during a half-cycle (or a 12 log reduction during a full cycle) is required.

Sporicidal effectiveness: A measure of the effectiveness of the sporicidal process and can be evaluated by comparing the number of microorganisms recovered from the test instruments to the recovery count. Sporicidal effectiveness can be expressed as a percent or log reduction. Typically, at least a 6 log reduction (99.9999%) of bacterial endospores during a half-cycle (or a 12 log reduction during a full cycle, i.e., a SAL of $10^{-6}$) is required.

Rinsing efficacy: The efficacy of a water rinsing process may be calculated by measuring the concentration (or parts per million) of chemical residues remaining on the instrument after rinsing with a copious volume of water.

Rinsing effectiveness: A measure of the effectiveness of the water rinsing process and can be evaluated by comparing the concentration (or parts per million) of chemical residues remaining on the test instruments after rinsing with water to the concentration (or parts per million) of chemical residues remaining on the control instruments.

Neutralizer: A reagent used to stop the antimicrobial activity of residual cleaning agent(s), disinfectant(s) and/or sterilant(s) that may be present on test instruments and eluted along with the target microorganisms.

British soil: Bovine serum (10 ml), saline (10 ml) and dry milk powder (6 grams).

DETAILED DESCRIPTION OF EXEMPLARY EMBODIMENTS

The method of the invention can be used to evaluate the efficacy of a decontamination process for instruments, such as endoscopes, artificially contaminated with mock organic soil tagged with recoverable target microorganisms. The method determines the efficacy of the decontamination process by simulating soiling that results from actual clinical conditions.

The method can also be used to verify the claims for a multi-step decontamination process, or this method can be applied to evaluate one or more particular phases of the process, including, but not limited to, pre-cleaning, manual cleaning, automated cleaning, chemical immersion and water rinsing.

The method is particularly suitable for reusable and immersible flexible fiberoptic and video gastrointestinal endoscopes and bronchoscopes.

The method preferably uses a resistant mycobacterium species to determine high-level disinfection or a bacterial endospore species to determine sporicidal efficacy. These target organisms are used as tracers, and quantification of their removal from the object (e.g., log reduction) by the decontamination process being evaluated provides a means for determining the efficacy of the decontamination process. Worst-case conditions are preferably implemented as part of the testing method.

After at least one control and test object (and preferably at least three test objects, but maybe as many as 5), such as an endoscope, has been contaminated with an inoculum wherein only the test objects are subjected to the decontamination process to be evaluated, the efficacy of the decontamination process is assessed using standard and validated microbiologic sampling techniques, including swabbing, flushing (elution), and brushing techniques. The effectiveness of the decontamination methods can be assessed by comparing target organisms recovered from control objects (preferably at least three) substantially identical (instruments are considered to be substantially identical for present purposes if, e.g., they are the same model produced by the same manufacturer) to target organisms recovered from test objects wherein the control objects have not been subjected to the decontamination process being evaluated.

The test and control objects are contaminated identically. That is, the same sites on each are contaminated with the same amount of inoculum employing identical inoculation techniques. Preferably, more than one test object site and more than one control object site are inoculated. It is also preferred that some of the test and control sites are on external surfaces of the test and control objects and the balance of the test and control sites are on internal surfaces of the test and control objects.

The inoculum comprises microorganisms, preferably mixed with an organic soil. Preferred microorganisms include *Bacillus stearothermtophilus* and *Mycobacterium terrae*. The organic soil can be, e.g., blood serum, and/or a mock organic soil, and is preferably British soil. The concentration of the microorganisms in the inoculum should be at least $10^8$ CFU/ml.

It is preferable to verify that the test and control object sites have been contaminated with the inoculum.

Cleaning is determined to be effective when the number of microorganisms recovered from the test object site(s) is about 3 logs less than the number of microorganisms recovered from the identical control object site(s). The mock soil is preferably tagged with microorganisms for counting.

Disinfection is determined to be effective when the number of microorganisms recovered from the test object site(s) is about 6 logs less than the number of microorganisms recovered from the identical control object site(s). The microorganisms are preferably mycobacteria.

Sterilization is determined to be effective when the number of microorganisms recovered from the test site(s) is preferably about 12 logs less than the number of microorganisms recovered from the identical control object site(s). The microorganisms are preferably bacterial endospores.

The efficacy of a decontamination procedure determined by the method of the invention can be compared with the efficacy of a different decontamination procedure also determined by the method of the invention.

The invention will be illustrated in more detail with reference to the following examples, but it should be understood that the present invention is not deemed to be limited thereto.

EXAMPLES

Equipment (1) Syringes, 10–15 ml, sterile
(2) Sterile cotton or Dacron swabs
(3) Sterile Petri dishes
(4) A test tube rack and sterile test tubes to hold 10 ml
(5) Sterile bottles to hold 50 ml
(6) Sterile flasks to hold 250–500 ml
(7) Ethylene oxide or other type of sterilizer for the medical instruments being examined. Alternatively, liquid chemical sterilants for high-level disinfection, such as 6% (or more) hydrogen peroxide or 2% glutaraldehyde.
(8) Water bath which can maintain temperature from 20–60±2° C.
(9) Incubator(s) which maintain 56° C. (for *Bacillus stearothermtophilus*)
(10) Membrane filters (0.45 mm) and filter supports
(11) Colony counter
(12) Various sizes of disposable (sterile) plastic pipettes
(13) Reusable medical instruments cleaned and high-level disinfected or sterilized prior to use. If an instrument is reused, it must be thoroughly cleaned and high-level disinfected or sterilized between each use.
(14) Accessory cleaning devices or apparatus to be used in the test cycle and/or for reprocessing between uses as specified by the manufacturer of the test instrument.
(15) Vortex mixer and/or sonicator
(16) Vacuum pump
(17) Inoculating loops
(18) Hewlett Packard 5890 gas chromatograph with flame ionization detector, and a Hewlett Packard 3396A integrator
(19) Scale, capable of 0.0001 gram accuracy

Materials and Reagents (1) Sterile USP Fluid D (elution fluid) containing Polysorbate 80 (Tween). Alternatively, sterile elution fluid solution containing 0.4 gram $KH_2PO_4$, 10.1 gram $Na_2HPO_4$, and 1.0 gram isooctyl phenoxypolyethoxy ethanol (Triton X- 100) prepared in 1 liter of Type III or better ASTM water adjusted to pH 7.8. Appropriate neutralizers may be added to either of these solutions.
(2) Soybean-Casein Digest Broth, USP, with an without appropriate neutralizers.
(3) Soybean-Casein Digest Agar, USP, single and double strength with and without appropriate neutralizers in 10–50 ml tubes or bottles tempered to 48±2° C.
(4) Sterile saline or phosphate buffer (for rinsing membrane filters).
(5) Sterile, purified water
(6) British soil

Culture Preparation

For high-level disinfection, five 7H11 plates maybe heavily swabbed with *Mycobacterium terrae* ATCC 15755

(or another appropriate mycobacterium species, such as, e.g., *Mycobacterium bovis*) from a stock culture plate and incubated at 35–39° C. for at least 10 days. The plates are harvested using a sterile loop. The harvested culture is suspended in sterile purified water and vortexed vigorously. The culture is ground in a tissue grinder with buffered gelatin and sonicated with a surfactant. The culture is mixed with British soil, and a standard plate count is performed on the inoculated British soil to assess the starting titre. The initial inoculum (in CFU) should be at least one the order of $10^8$ CFU in order to permit recovery of at least $10^6$ CFU during testing.

Alternatively, standardized suspensions of *Bacillus stearothermtophilus* endospores (or another suitable endospore, such as, e.g., *Bacillus subtilis*) meeting USP resistance criteria for steam sterilization, can be used. The origin of the spore strain, production, storage, and expiration dates should be identified. Bacterial endospores are preferred as the target strain because they are more resistant to potential microbiocidal effects of the cleaning solutions.

Type III or better ASTM water, is used for making broth and elution fluids (see ASTM Standard D1193). When a water-rinse step is part of the decontamination procedure, at least bacteria-free water is used.

The appropriate cleaning solution(s) and neutralizer(s) are used in accordance with the decontamination method being evaluated.

Evaluation Method

All test endoscopes are cleaned and high-level disinfected/sterilized and dried, per manufacturer's instructions, before each test. All detergents and liquid chemical sterilants used during testing are used in accordance with the manufacturer's instructions.

The microorganisms are mixed with a volume of British soil and the inoculum is applied to each control instrument (i.e., instruments not subjected to the test cycle, which are used to determine the recovery count) and test instrument (i.e., instruments subjected to the prescribed test cycle). Preferably, the inoculum is applied to a plurality of sites on each instrument. It is particularly preferred to apply the inoculum to a plurality of internal sites and a plurality of external sites on each instrument.

Appropriate microbiologic methods (e.g., routine plating procedures with appropriate agar media) are employed to determine the initial starting titre (in CFU/ml). An inoculum that contains at least $10^8$ CFU is necessary to permit recovery of at least $10^6$ CFU.

The volume of British soil inoculated onto each site on the instruments depends on the clinical application. For each endoscope channel, the volume of British soil including the target organisms should equal that volume encountered clinically in that channel (i.e., that percentage of the suction channel's void volume, as supported by data, e.g., 30%). A similar approach should be employed for the endoscope's other channels and surfaces.

Validated control experiments are preferred to confirm that the British soil does not adversely affect (e.g., destroy) the target microorganisms. Similarly, validated control experiments are preferred to confirm that any detergent used during testing does not adversely affect the target microorganisms.

Sites to be inoculated include, but are not limited to, at least one endoscope channel; the biopsy inlet; the suction and air/water cylinders; the suction and air/water valve buttons; and the endoscope's exterior, including its insertion tube, umbilical cord, control head and knobs. Emphasis should be placed on contaminating those sites which are most difficult to access and clean (e.g., a duodenoscope's elevator-cable channel).

In order for the test to be valid, each of the above sites must be contaminated using a validated method that ensures that at least $10^6$ CFU can be recovered from the respective control instruments' sites.

The following is a non-limiting example of a suitable method for inoculating an endoscope. The suction channel and air/water channel at the inlet ports on the umbilical head are inoculated. The biopsy and elevator wire channels at the inlet ports on the control head are also inoculated. The inoculum is spread through each channel from the site of inoculation to the distal tip using pressurized air. Care should be taken to ensure that all of the inoculum remains in the channels. The insertion tube from its distal tip to the "6" depth mark is inoculated using a Dacron tipped applicator saturated with the inoculated British soil. The Dacron swab is also used to inoculate the internal surfaces of the biopsy inlet port, air/water valve cylinder, and suction valve cylinder. The air/water valve and suction valve from the endoscope are removed and separately inoculated with a saturated Dacron swab. Particular attention should be paid to the area of the suction valve that is only accessible by activating the suction button. After inoculation, the endoscope is allowed to dry thoroughly.

Because of the complexity of flexible endoscopes and the desire to evaluate a representative sample of a particular model of instrument, the method of the invention should be performed with at least 3, and preferably 5, test and control replicates. Repeating the method of the invention at least 3, and preferably 5, times with one instrument (rather than one replicate from each of 3 or 5 instruments) is also a preferred method, since it can minimize the effects of certain experimental errors.

A complete test cycle is performed using the instrument manufacturer's and/or automatic to processor manufacturer's directions for cleaning, disinfecting, sterilizing and/or water-rinsing the test instruments inoculated with the target organisms mixed with British soil or another mock soil. The efficacy of a complete decontamination procedure or of any number of steps thereof, can be evaluated.

Control experiments are performed to ensure that the cleaning agent does not injure or destroy the target organisms. Detergents that are sporicidal or mycobacteriocidal as employed in the test cycle may not be appropriate for this test method. Suitable detergents include, e.g., chemical detergents, such as Tergal 800 (Custom Ultrasonics, Inc., Ivyland, Pa.), or an enzymatic detergent formulation, such as Medzyme (PEA Products, Inc., Hunt Valley, Md.) or Endozime (Ruhof Corp., Valley Stream, N.Y.).

Worst case conditions must be clearly defined and include, but are not limited to, the following (see also the United States Food and Drug Administration publication "Guidance on the content and format of pre-market notification [510(k)] submissions for liquid chemical germicides" to ensure all necessary worst-case criteria have been satisfied). When evaluating the efficacy of a cleaning, disinfection and/or sterilization process, the instrument should not be manually pre-cleaned after inoculation of the endoscope. A sufficient organic-soil challenge (e.g., 5–10% v/v bovine calf serum), which is independent from the British soil mixed with the microorganisms, is added to the volume of liquid chemical sterilant to reduce its efficacy. Prior to testing, the sterilant is diluted with water until its concentration equals its MEC (minimum effective concentration). All tests are performed on or near the expiration date of the sterilant's active use-life (e.g., 14 days). Similarly, the detergent is diluted with water to its MEC and used at the end of its use-life, if appropriate. The foregoing conditions are necessary to simulate worst-case conditions. The British soil mixture used to contaminate the endoscope must have thoroughly dried before beginning testing.

When the method of the invention is used to evaluate a decontamination method in general, as opposed to evaluating a method for decontaminating a particular item, it is preferred that the type of object to be decontaminated in the evaluation process have a physical design which poses a significant challenge to the decontamination method (e.g., the side-viewing duodenoscope).

The following describes general techniques for recovering organisms from both control and test endoscopes.

Validated sampling techniques, which include swabbing, flushing, and brushing using an appropriately sized sterile brush, are required to recover the target microorganisms from each inoculated site. It is impractical to determine bioburden by immersion of flexible endoscopes in growth medium because of their complexity, size, and difficulty in long-term incubation or deleterious effects from immersion and incubation. Each of the control and test endoscopes' sites are, to the extent possible, flushed, swabbed or brushed, and flushed again. The recovered bioburden is the sum of these three topics.

Those sites whose design precludes direct swabbing or brushing to recover bioburden, such as most of the endoscope's internal channels, are aseptically irrigated with a volume of sterile fluid preferably equal to at least 3 times and void volume of the channel. Alternatively, this flushing procedure is repeated as many times as necessary to recover substantially all organisms using fresh sterile fluid. The number of flushes and the volume of each flush necessary to recover all organisms is preferably validated. For each channel, the recovered elution fluids (i.e., effluent) is preferably mixed using a vortex mixer. Serial 10-fold dilutions or membrane filtration is preferably performed to prepare for plate counting. The samples are subcultured and enumerated.

Control endoscopes are necessary to determine the number of target organisms that can be recovered from each instrument site (recovery count). The test cycle is not performed on the control instruments. The difference between the number of organisms inoculated onto the site and the number recovered from that site is the number of microorganisms that cannot be recovered from that site.

Alternatively, the number of unrecoverable organisms remaining inside the endoscope can be determined knowing the initial staring titre (CFU/ml), the volume of the initial inoculum applied to the site, and the number of recovered target organisms (e.g., calculation of the recovery efficiency).

A minimum of 3 control instruments are evaluated using 3 replicates from 1 instrument. As few as 3 replicates can be used, but only if shown to yield results similar to 5 replicates.

After brushing and/or swabbing, the brush and/or swab are preferably each placed in a bottle containing purified sterile water and shaken to dislodge any adhering target microorganisms. The shaking procedure is validated to determine how many organisms are dislodged by this method. See, e.g., Bond et al., "Microbiological Culturing of Environmental and Medical-Device Surfaces," in *Clinical Microbiological Procedures Handbook*, Section 11: Epidemiologic and Infection Control Microbiology, pp. 11.10.1–11.10.9 (Isenberg et al. eds., Am. Soc. Microbiol., Washington, D.C., 1992).

All portions of the endoscope that can be removed, such as the suction and air/water valve buttons, are preferably placed in a bottle containing purified sterile water and shaken for as long as necessary to dislodge all target organisms. This shaking procedure must be validated to ensure all organisms are dislodged by this method.

The following is a non-limiting example of a method for recovering organisms from test and control endoscopes. Each channel of the endoscope is preferably flushed with a triple volume of sterile water, and the effluent from each channel is collected in its own sterile bottle. Alternatively, the suction channel and air/water channel at the inlet ports on the umbilical head are flushed with fresh sterile fluid as many times as necessary to recover all organisms. The number of flushes necessary to recover all organisms is preferably validated.

The biopsy and elevator wire channels at the inlet ports on the control head are flushed. Each channel from the flush site to the distal tip is flushed with sterile water followed by pressurized air. An appropriately-sized endoscope cleaning brush is used to brush the biopsy and suction channels after the flushing procedure, as well as to brush the biopsy inlet port, suction valve cylinder, and air/water cylinder. The brushes are immersed in separate bottles of sterile water and extracted with shaking. The suctions valve and air/water valve are immersed in sterile water and extracted with shaking. This shaking method is validated to ensure substantially all of the microorganisms were recovered.

A Dacron tipped applicator saturated with sterile water is used to recover the organisms that remain on the insertion tube of the endoscope. The number of wipes of the surface using the swab necessary to recover all the microorganisms is determined. The swab is immersed in sterile, purified water and extracted with shaking. This shaking method is validated to ensure that all of the microorganisms are recovered.

For each site, the organism recovery steps are repeated at least 3 times to determine a statistically meaningful data.

Aliquots of the extract fluid are diluted when necessary. The diluted aliquots are either directly plated onto 7H11 plates or filtered through 0.45 $\mu$m membranes, which are then placed on 7H11 agar plates. The plates are incubated at 37±2° C. for at least 10 days (until colonies form which are large enough to count) and the organisms are enumerated. A total of at least three replicates are performed for the positive controls. The number of target microorganisms recovered from the control and test instruments are determined using either the serial dilution or membrane filtration method.

By comparing the number of organisms recovered from the test instruments to the number recovered from the control instruments, the efficacy of the decontamination process can be calculated.

Total Organic Carbon Test: Optionally, a total organic carbon test, which measures the amount of organic carbon (British soil) remaining in the endoscope after cleaning can be used for the cleaning process to corroborate the microbial log reduction. Because the British soil Is uniformly mixed with target microorganisms, the measured percent reduction of carbon, using the total organic carbon test, should equal the percent reduction of the target organisms measured using the flushing, brushing and swabbing techniques described above.

A 10 parts per million control is made using potassium hydrogen phthalate. This control is injected three times into the analyzer. A mean and standard deviation are calculated from these three replicates. Using this mean value, the analyzer is calibrated to a correction coefficient of at least 0.99.

Neutralization Test: Tests are performed to show that the neutralizers used during testing stop the antimicrobial action of the detergent and chemical sterilant, and that neither is inhibitory to the germination or growth of the target organisms. For example, tests can be performed to determine whether the triple rinse and agar are sufficient to neutralize residual germicide present after recovery of the organisms.

A *Mycobacterium terrae* ATCC 15755 culture is diluted to $10^3$ CFU/ml. A plate count is performed on this dilution used for the test. A fresh solution of the disinfectant is diluted to approximately 100 times the residual level detected after water rinsing.

Three membrane filtration funnels with 0.45 micron filters are prepared and approximately 10 ml of sterile purified water are filtered to wet the membranes. 100 ml of the diluted disinfectant solution are filtered through each membrane, followed by 2 ml of *M. terrae* through each membrane, without rinsing between the diluted disinfectant solution and the culture. Three 100 ml rinses of purified water are then rinsed through each membrane. The membranes are placed on 7H11 agar and incubated at 37±2° C. for 14 days. The organisms are then enumerated.

Injured cell recovery test: This test is performed to demonstrate that injured target organisms can be recovered by the employed organism recovery techniques.

*M. terrae* ATCC 15755 culture is preferably diluted to $10^5$ CFU/ml. A fresh solution of the sterilant is diluted to approximately 1×, 100× and 1000× the detected residual level after water rinsing. 100 ml of sterile purified water and 100 ml of each of the diluted sterilant solutions are placed into a water bath and equilibrated to 25±1° C. 1 ml of the $10^5$ CFU/ml culture of *M. terrae* is added to each solution and incubated therein for 45 minutes. After the exposure period, an aliquot of the neutralizer sufficient to neutralize the sterilant is added to each solution.

An aliquot of 0.1 ml, 1.0 ml, and 10 ml is filtered for each solution and the membranes are placed on 7H11 agar. The agar is incubated at 37±2° C. for 14 days, followed by enumeration of the organisms.

Phenol resistance test: This test is performed to determine the resistance to phenol of the culture after various incubation times (i.e., culture age) and culture preparation methods. This is necessary to determine the effect of age on microbial resistance.

Three 7H11 plates are heavily swabbed with *M. terrae* ATCC 15755 from a stock culture plate and incubated at 35°–39° C. One plate is pulled from the incubator at 10 days, 15 days, and 20 days. The plates are harvested using 5 ml of purified water and a "hockey stick" to remove the growth. 1 milliliter of each harvested culture is ground for 1 minute in a tissue grinder with 1 ml of sterile buffered gelatin.

Ground and ungrounded cultures from each incubation time are tested for phenol resistance by placing 1 ml of culture in 9 ml of a 0.8% phenol solution equilibrated in a water bath set at 25±0.5° C. 1 milliliter of each culture is also placed into 9 ml of lethene broth equilibrated in a water bath set at 25±0.5° C. to serve as the positive control. The cultures are exposed to the phenol (or lethene for controls) for 20 minutes at 25±0.5° C., then 1 ml is removed and added to 9 ml of lethene broth. The cultures are serially diluted in lethene broth and plated on 7H11 agar. The plates are incubated for 10 days at 35°–39° C. and the colonies are enumerated. The log reduction is then calculated.

Water rinsing efficacy: Tests to confirm the adequacy of the water rinse phase, which is the phase following the cleaning and/or chemical immersion phase, should be performed.

Each of the endoscope's inoculated sites are evaluated to detect the presence of residual chemical sterilants after water rinsing.

Standards for the liquid sterilant are prepared weight to weight in milligrams per milliliter (mg/ml). A Hewlett Packard 5890 with flame ionization detector is used for chromatographic analyses. The detector responses arc integrated with a Hewlett Packard 3396A integrator. Three microliter samples are injected and extrapolated with the standards to assess peak area for the residual.

The endoscope's channels are flushed with a triple volume of sterile, purified water, and the effluent is analyzed to determine the presence of chemical residues. The sterilant sample residual levels are assessed by multiplying the parts per million (micrograms/micrometer) from integrated peak areas by the volume of extraction.

Chemical sterilant concentration: Using the method just discussed, the concentration of the liquid sterilant is measured and recorded before each test.

Example of Simulated-Use Test

This simulated-use test protocol evaluates the effectiveness of a decontamination process for reusable medical instruments artificially contaminated with a mock organic soil, such as British soil, tagged with target microorganisms. This protocol is designed primarily for reusable and immersible flexible fiberoptic and video gastrointestinal endoscopes and bronchoscopes, but can be applied to other types of reusable medical instruments. The endoscopes used during testing should be identified by their manufacturer, name, model, and serial number. The condition of the endoscope (new, used) should also be noted.

The test method recommends use of a mycobacterium species to determine high-level disinfection (or a bacterial endospore to determine sporicidal) effectiveness. The resistance of the selected mycobacteria species should be comparable to that of *Mycobacterium tuberculosis*. These microorganisms are used as tracers, and quantification of their removal (e.g., log reduction) provides a means for determining the effectiveness of a decontamination process. The target organism's genus, species, and all other necessary information should be recorded, as well as the ingredients of the mock organic soil used to simulate patient debris.

This test protocol is intended to determine the effectiveness of a decontamination process by simulating worst-case clinical in-use conditions. This protocol may be used to verify the claims of a complete decontamination process, or this protocol may be limited to any one particular phase of the process, such as cleaning or disinfection.

Worst-case conditions should be clearly defined.

This test protocol is designed primarily for manufacturers of reusable medical instruments, detergents, and liquid chemical germicides. However, this protocol may be utilized by health care facilities seeking to assess the effectiveness of a decontamination process. Knowledge of microbiological and aseptic techniques and a familiarity with the designs of the instruments is required to conduct this simulated-use test. The recovery of surviving microorganisms is assessed using validated microbiologic techniques, including swabbing, flushing (elution), and brushing techniques, per the recommended guidelines. The effectiveness of the elution, swabbing, and brushing methods needs to be validated. This can be accomplished, in part, by comparing the recovery of target organisms from the test instruments to the recovery of target organisms from the control instruments.

This test protocol may involve hazardous materials, operations, and equipment. This method does not purport to address all of the safety problems associated with its use. It is the responsibility of the user of this test method to establish appropriate safety and health practices.

A skilled artisan would refer to an appropriate microbiology reference source for the necessary equipment. Reusable medical instruments, such as flexible endoscopes are cleaned and are high-level disinfected or sterilized prior to use. If an instrument is used repeatedly, it must be thoroughly cleaned and high-level disinfected or sterilized between uses. Several different types of endoscope models are recommended. Accessory cleaning devices or apparatuses to be used in the test cycle and/or for reprocessing between uses as specified by the manufacturer of the test instrument.

A skilled artisan would refer to an appropriate microbiology reference source for the necessary materials and reagents. A culture is prepared.

For high-level disinfection, heavily swab five 7 H 11 plates with *Mycobacterium terrae* ATCC 15755 (or another appropriate mycobacterium species) from a stock culture plate and incubated at 35°–39° C. for at least 10 days. Harvest the plates using a sterile loop. Suspend the harvested culture in sterile purified water and vortex it vigorously. Grind the culture in a tissue grinder with buffered gelatin and sonicate it with a surfactant. Mix the culture with British soil, and perform a standard plate count on the inoculated British soil to assess the starting tier. The inoculum should be at least on the order of $10^8$ CFU to permit recovery of at least $10^6$ CFU during testing.

Alternatively, standardized suspensions of *B. stearothermophilus* endospores (or another suitable endospore) meeting USP resistance criteria for steam sterilization may be used. The origin of the spore strain, production, storage, and expiration dates should be identified. (Bacterial endospores may be most suitable as the target strain because they would be more resistant to potential microbiocidal effects of the cleaning solutions.)

Type III or better ASTM water, for making broth and elution fluids (see Specification D1193). Use at least bacteria-free water, when a water-rinse step is part of the cleaning process. Use the appropriate cleaning solution (i.e., one that does not injure the microorganisms). Use the appropriate neutralizers.

All test endoscopes must be cleaned and high-level disinfected/sterilized per manufacturer's instructions, before each test. All detergents and liquid chemical germicides used during testing should be used in accordance with their respective labels.

The instruments are inoculated. Mix the microorganisms with a known volume of British soil (or equivalent) and apply the inoculum to both the control and test instruments. (A concentration of microorganisms, such as the starting titre)*(a volume of inoculum)=(A known number of microorganisms). The volume of British soil inoculated onto the instrument depends on the clinical application. For each endoscope channel, the volume of British soil, mixed with the target organisms, should equal that volume encountered clinically in that channel. A similar approach should be employed for the endoscope's other channels and surfaces. Employ appropriate microbiologic methods (e.g., routine plating procedures with appropriate agar media) to determine the starting titre (in CFU/ml).

Sites to be inoculated should include, but are not limited to:
  each endoscope channel;
  the biopsy inlet;
  the suction and air/water cylinders;
  the suction and air/water valve buttons; and
  the endoscope's exterior, including its insertion tube, control head and knobs.

Emphasis should be placed on contaminating those sites that are most difficult to access and clean (e.g., the duodenoscope's elevator-cable channel).

In order for the test to be valid, each of the above sites must be contaminated using a validated method that ensures that at least $10^6$ CFU can be recovered from the respective control instrument's site. Each site should therefore be contaminated with a suspension that contains at kit least $10^8$ CFU. The following is a sample method for inoculating the endoscope (although an alternative method may be more appropriate.

Inoculate the suction channel and air/water channel at the inlet ports on the umbilical head. Inoculate the biopsy and elevator wire channels on the inlet ports on the control head. Spread the inoculum through each channel from the site of inoculation to the distal tip using pressurized air. Ensure that all of the inoculum remains in the channels. Inoculate the insertion tube from its distal tip to the "6" depth mark using a Dacron tipped applicator saturated with the inoculated British soil. Also, use the Dacron swab to inoculate the internal surfaces of the biopsy inlet port, air/water valve cylinder, and suction valve cylinder. Remove the air/water valve and suction valve from the endoscope and separately inoculate them with a saturated Dacron swab. Particular attention should be paid to the area of the suction valve that is only accessible by activating the suction button. After inoculation, allow the endoscope to dry thoroughly.

Because of the complexity of flexible endoscopes, 5 test and control replicates are recommended (although 3 may be sufficient, depending on the standard deviation). Five replicates using one instrument is also recommended (rather than one replicate from five instruments). After inoculation, the instrument should remain dormant for 30 minutes (or the appropriate time necessary to permit thorough drying and hardening of the British soil inside the endoscope's internal channels).

Perform a complete test cycle, exposing the test instruments to be specified decontamination process. The effect of any single phase may be evaluated.

Validated control experiments should be performed to ensure that any detergent used during testing does not injure or destroy the target organisms. Detergents that are sporicidal or mycobacteriocidal may not be appropriate for this test method. Validated control experiments should be performed to ensure that the British soil (or equivalent) does not adversely affect (i.e., injure) the target microorganisms. A validated method will need to be developed, based on a definition of "dry," to determine whether 30 minutes is sufficient to dry the instrument's internal channels.

Worst case conditions should be clearly defined and include, but not be limited to, the following (refer to the FDA 510(k) draft guidance article for liquid chemical sterilants/high-level disinfectants) to ensure all necessary worst-case criteria have been satisfied:

a) A sufficient organic-soil challenge (e.g., 5–10% v/v bovine calf serum) should be added to the liquid chemical sterilant to reduce its efficacy;
b) Prior to testing, the sterilant should be diluted with sterile water until its concentration equals its MEC (minimum effective concentration). Similarly, the detergent should be diluted with water and used at the end of its use-life, if appropriate, to simulate worst-case conditions.
c) All tests should be performed on or near the expiration date of the sterilant's active use-life (e.g., 14 days);
d) The British soil, mixed with microorganisms, that is used to contaminate the endoscope should be dry inside the endoscope's channels before testing proceeds; and
e) Justification for the type of instrument (e.g., side-viewing duodenoscope) chosen for testing should be provided to ensure that its physical design poses a significant challenge.

All of the sampling techniques, which likely include swabbing, flushing, and brushing, should be validated to determine the recovery efficiency of each technique. For example, one technique may only be able to recover 50% of the starting titre, while another technique may recover 95%. Also, it is impractical to determine bioburden by immersion of flexible endoscopes in growth medium because of their complexity, size, and difficulty in long-term incubation or deleterious effects from immersion and incubation.

Each of the control and test endoscopes' sites should be flushed, swabbed or brushed, if appropriate. The recovered bioburden is the sum of these steps. Those sites whose design precludes direct swabbing or brushing to recover bioburden, such as the endoscope's internal channels, should be aseptically irrigated with a volume of sterile elution fluid equal to at least 3 times the void volume of the channel. Each channel should be sampled separately. Repeat this flushing procedure as many times as necessary using fresh elution fluid. It will be necessary to validate the number of flushes necessary to recover the microorganisms. Depending on the technique, it may not be possible to recover every microorganism. For each channel, mix and recover the elution fluid using a Vortex mixer. Prepare for plate counting using either serial 10-fold dilutions or membrane filtration. Subculture and enumerate.

Control endoscopes are necessary to determine, for example, the efficiency of each sampling technique i.e., the number of target organisms that can be recovered from each instrument site. The number of unrecoverable microorganisms remaining on the instrument's site after sampling can be determined by subtracting the number of recovered microorganisms from the number of microorganisms inoculated onto the site. (The number of microorganisms inoculated onto the site equals: the starting titre multiplied by the volume of inoculum applied to the site.) At least $10^6$ target organisms must be recoverable from each 'control' site (e.g., each channel) for the test to be valid.

A minimum of 3 to 5 control and test instruments should be evaluated using replicates from one instrument or one replicate from several instruments. As few as 3 replicates may be used, but only if shown to yield results similar to 5 replicates. After brushing and/or swabbing, the brush and/or swab are each placed in a bottle containing purified sterile water and shaken to dislodge any adhering target microorganisms. As well as determining the efficiency of the brushing and swabbing techniques, it will be necessary to validate the shaking procedure, manual or automated, to determine the number or organisms that remain on the brush or swab and cannot be recovered (i.e., its efficiency).

All portions of the endoscope that can be removed, such as the suction and air/water valve buttons, should be separately sampled. The technique might involve placing a valve in a bottle containing purified sterile water and shaking the bottle to dislodge all target organisms. It will 20 be necessary to validate the shaking procedure to determine its extraction efficiency. The following is a sample method for recovering organisms from the test and control instruments (although an alternative method may be more appropriate):

Flush each channel of the endoscope with a triple volume of sterile water, and collect the effluent in a sterile bottle. Flush the suction channel and air/water channel at the inlet ports on the umbilical head. Repeat this flushing procedure as many times as necessary using fresh elution fluid. It will be necessary to validate the number of the flushes necessary to recover the organisms. Do not mix the effluent collected from each channel. Analyze each separately.

Flush the biopsy and elevator wire channels at the inlet ports on the control head. Use an appropriately-sized endoscope cleaning brush to brush the biopsy and suction channels after the flushing procedure, as well as to brush the biopsy inlet port, suction valve cylinder, and air/water cylinder. Immerse the brushes in separate bottles of sterile water and extract with ED shaking using a validated process. Finally, flush those sites that were brushed, per the flush-brush-flush method. Immerse the suction valve and air/water valve in sterile water and extract with shaking. It will be necessary to validate this shaking method to ensure the microorganisms were recovered.

Use a Dacron tipped applicator saturated with sterile water to recover the organisms that remain on the insertion tube of the endoscope. It will be necessary to determine how many wipes of the surface using the swab are necessary to ensure all of the microorganisms were recovered. Immerse the swab in purified water and extract with shaking. It will be necessary to validate this shaking method to ensure all of the microorganisms were recovered.

Dilute aliquots of the extract fluid when necessary. Either directly plate them onto 7H11 plates or filter them through 0.45 µm membranes. Place the membranes on 7H11 agar plates. Incubate the plates at 37±2° C. for at least 10 days (until colonies were large enough to count) and enumerate the organisms. Perform a total of at least three replicates.

The number of target microorganisms recovered from the control and test instruments are determined using either the serial dilution or membrane filtration method. By comparing the. number of organisms recovered from the test instruments to the number recovered from the control instruments, the efficiency of the decontamination process can be calculated.

An optional total organic carbon test, which measures the amount of organic carbon (British soil) remaining in the endoscope after cleaning and/or disinfection, can be used to corroborate the microbial log reduction. Because the British soil is uniformly mixed with the target microorganisms, the measured percent reduction of carbon, using the total organic carbon test,. should equal the percent reduction of the target organisms measured using the flushing, brushing and swabbing techniques described above. Briefly, make a 10 parts per million control using potassium hydrogen phthalate. Inject this control three times into the analyzer. A mean and standard deviation is calculated from these three replicates. Using this mean value, the analyzer is calibrated to a correlation coefficient of at least 0.99. This test may require equipment not readily available, and hence is not recommended.

Perform the necessary tests to show that the neutralizer used during testing stops the antimicrobial action of the chemical sterilant (and detergent, if appropriate), but is not inhibitory to the germination or outgrowth of the target organisms. For example, it may be necessary to demonstrate that the triple rinse and agar are sufficient to neutralize residual germicide present after recovery of the organisms. To demonstrate that the triple rinse and 7H11 agar were sufficient to neutralize any residual glutaraldehyde present after organism recovery, a neutralization assay will need to be performed.

By example, dilute a *Mycobacterium terrae* ATCC 15755 culture to $10^3$ CFU/ml. Perform a plate count on this dilution used for the test. Dilute a fresh solution of the disinfectant to approximately 100 times the residual level detected after water rinsing. Prepare 3 membrane filtration funnels with 0.45 micron filters and approximately 10 ml of sterile purified water were filtered to wet the membranes. Filter one hundred ml of this diluted disinfectant solution through each membrane. Filter 2 ml of *M. Terrae* through each membrane without rinsing between the diluted disinfectant solution and the culture. Perform three 100 ml rinses of purified water for each membrane. Place the membranes on 7H11 agar and incubate them at 37±2° C. for at least 14 days. Enumerate the organisms.

An injured cell recovery test is necessary to demonstrate that injured target organisms can be recovered by the employed organism recovery techniques. By example, dilute a *M. terrae* ATCC 15755 culture to $10^5$ CFU/ml. Dilute a fresh solution of the sterilant to approximately 10×, 100×, and 1000× the detected residual level after water rinsing. Place 100 ml of sterile purified water and 100 ml of each of the diluted sterilant solutions into a water bath and equilibrated to 25±1° C. Add one ml of the $10^5$ CFU/ml culture of *M. terrae* to each solution and set a timer for 45 minutes. After the exposure period, add a calculated aliquot of the neutralizer to each solution. Filter an aliquot of 0.1 ml, 10 ml for each solution and place the membranes on 7H11 agar. Incubated at 37±2° C. for at least 14 days and enumerate the organisms.

A phenol resistance test is performed to determine the resistance to phenol of the culture after various incubation times (i.e., culture age) and culture preparation methods. This is necessary to determine the effect of age on microbial resistance.

By example, heavily swab three 7H11 plates with *M. terrae* ATCC 15755 from a stock culture plate and incubate at 35°–39° C. Pull one plate from the incubator at 10 days, 15 days, and 20 days. Harvest the plates using 5 ml of purified water and a hockey stick to remove the growth. Grind 1 milliliter of each harvested culture for 1 minute in a tissue grinder with 1 ml of sterile buffered gelatin.

Test ground and ungrounded cultures from each incubation time for phenol resistance by placing 1 ml of culture in 9 ml of a 0.8% phenol solution equilibrated in a water bath set at 25±0.5° C. Also, place 1 milliliter of each culture into 9 ml of lethene broth equilibrated in a water bath set at 25±0.5° C. to serve as the positive control. Expose the cultures to the phenol (or lethene for controls) for 20 minutes at 25±0.5 ° C., then remove 1 ml and add it to 9 ml of lethene broth. Serially dilute the cultures in lethene broth and plate on 7H11 agar. Incubate the plates for 10 days at 35°–39° C. and enumerate colonies. Calculate the log reduction.

If appropriate, tests to confirm the adequacy of the water rinse phase (i.e., how well it removes chemical residues), which is the phase which typically follows the chemical immersion phase, may be necessary to perform. Each of the endoscope's inoculated sites should be evaluated to detect the presence of residual chemical sterilants after water rinsing.

By example, standards for the liquid sterilant were prepared weight to weight in milligrams per milliliter (mg/ml). A Hewlett Packard 5890 with flame ionization detector was used for chromatographic analyses. The detector responses were integrated with a Hewlett Packard 3396 A integrator. Three microliter samples were injected and extrapolated with the standards to assess peak area for the residual. The endoscope's channels were flushed with a triple volume of sterile, purified water, and the effluent was analyzed to determine the presence of chemical residues. The sterilant samples residual levels were assessed by multiplying the parts per million (micrograms/micrometer) from integrated peak areas by the volume of extraction.

Using an appropriate method, measure and record the concentration of the liquid sterilant before each test.

The use of control instruments can overcome the limitations described above regarding decontamination procedures that do not use control instruments. Thus, making erroneous 5 conclusions can be prevented. By way of example, a known concentration of the inoculum of microorganisms is applied to the internal surfaces of both the test and control instruments. After inoculation, a sterile fluid is rinsed through one end of each of the test and control instruments through their lumens and collected aseptically at the other end of the lumens. The sterile fluid from both the control and test instruments are analyzed microbiologically. The efficacy of the decontamination process is assessed by measuring and comparing the number of recovered microorganisms from the test instrument to the number of microorganisms recovered from the control instrument regardless of the number of microorganisms initially applied to the lumen surfaces, which may be significantly greater. In fact, the number of microorganisms recovered from the control instrument may be significantly less than the number of microorganisms initially applied to the lumen surfaces. By way of example, assume that the rinsing fluid from the control instrument is sterile.

Several factors contribute to this unexpected, though plausible result. None of these factors can be attributed to the decontamination process. One factor is the limitation of the rinse sampling method which prevents recovery of viable organisms inoculated on to the lumen surfaces. Also, due to limitations in the inoculation process, some of the microorganisms might have escaped and never have contaminated the lumen surfaces. Further, some of the microorganisms originally inoculated onto the lumen surfaces may have died naturally due to drying and not the decontamination process.

The use of controls eliminates the contribution of these factors and then associated errors to the sampling data. Thus, using control instruments allows the efficacy of any decontamination process to be described more accurately. As described above, the inability to recover microorganisms in the rinsing fluid may be caused by factors unassociated with the decontamination process. Thus, using control instruments is advantageous.

The invention has been described by way of example only and should not be construed by such examples as limiting in any manner. Particularly, the invention has been described in detail and with reference to specific examples thereof. It will be apparent to one skilled in the art that various changes and modifications can be made herein without departing from the spirit and scope of the invention.

What is claimed is:

1. A method for determining an efficacy of a decontamination procedure, the method comprising the steps of:

providing at least one test object and at least one control object;

contaminating multiple sites on each of the at least one test object and the at least one control object with a known amount of an inoculum comprising organisms;

performing the decontamination procedure on the at least one test object but not on the at least one control object;

recovering the microorganisms from each of those respective contaminated sites on the at least one decontaminated test object and the at least one contaminated control object;

comparing a number of microorganisms recovered from each respective site of the at least one decontaminated test object with a number of microorganisms recovered from each respective site of the at least one contaminated control object; and deeming the decontamination procedure effective when the number of microorganisms recovered from each site of the test object is at least approximately a 3 log reduction of the number of microorganisms recovered from each respective site of the control object.

2. The method of claim 1, wherein said at least one test object and said at least one control object are substantially identical prior to performing said method.

3. The method of claim 2, wherein said at least one test object and said at least one control object are surgical instruments.

4. The method of claim 2, wherein some of said test and control sites are on external surfaces of said test and control objects and a balance of said test and control sites are internal surfaces of said test and control objects.

5. The method of claim 2, wherein said at least one test object and said at least one control object are endoscopes.

6. The method of claim 2, further comprising verifying that said at least one test object site and said at least one control object site have been contaminated with said inoculum.

7. The method of claim 1, wherein at least three of said test object and at least three of said control object are provided.

8. The method of claim 1, wherein said inoculum further comprises an organic soil.

9. The method of claim 8, wherein said organic soil contains blood serum.

10. The method of claim 9, wherein said microorganisms are selected from the group consisting of *Bacillus stearothermophilus* and *Mycobacterium terrae*.

11. The method of claim 10, wherein an amount of said microorganisms in said known amount of inoculum is at least $10^8$ CFU.

12. The method of claim 1, wherein said inoculum further comprises British soil.

13. The method of claim 12, wherein said microorganisms are selected from the group consisting of *Bacillus stearothermophilus* and *Mycobacterium terrae*.

14. The method of claim 13, wherein an amount of said microorganisms in said known amount of inoculum is at least $10^8$ CFU.

15. The method of claim 1, wherein said microorganisms are selected from the group consisting of *Bacillus stearothermophilus* and *Mycobacterium terrae*.

16. The method of claim 15, wherein an amount of said microorganisms in said known amount of inoculum is at least $10^8$ CFU.

17. The method of claim 1, wherein an amount of said microorganisms in said known amount of inoculum is at least $10^8$ CFU.

18. The method of claim 1, wherein said decontamination procedure is cleaning, and said cleaning is determined to be effective when said number of microorganisms recovered from each respective site of said at least one test object is about 3 logs less than said number of microorganisms recovered from each respective site of said at least one control object.

19. The method of claim 18, wherein said known amount of inoculum is tagged for counting.

20. The method of claim 1, wherein said decontamination procedure is disinfection, and said disinfection is determined to be effective when said number of microorganisms recovered from each respective site of said at least one test object is about a 6 log reduction of said number of microorganisms recovered from each respective site of said at least one control object.

21. The method of claim 20, wherein said microorganisms are resistant mycobacteria.

22. The method of claim 1, wherein said decontamination procedure is sterilization, and said sterilization is determined to be effective when said number of microorganisms recovered from each respective site of said at least one test object is about a 12 log reduction of said number of microorganisms recovered from each respective site of said at least one control object.

23. The method of claim 22, wherein said microorganisms are bacterial endospores.

24. The method of claim 1, wherein said efficacy of said decontamination procedure is compared with said efficacy of a different decontamination procedure determined by said method.

25. A method for determining the efficacy of a decontamination procedure, comprising the steps of:

providing at least one test instrument and at least one control instrument, said instruments being substantially identical and having a plurality of multiple sites comprising internal and external sites in or on which microorganisms reside;

contaminating said multiple sites of said test instrument with a first known starting amount of inoculum comprising microorganisms and contaminating said multiple sites of said control instrument with a second known starting amount of the same inoculum, the first known starting amount of inoculum and the second known starting amount of inoculum being substantially the same, said contamination being applied to all said sites associated with said test and control instruments;

performing a decontamination procedure on said contaminated sites of said test instrument but not on said contaminated sites of said control instrument;

separately recovering microorganisms from each of those respective contaminated sites associated with said decontaminated test instrument and said contaminated control instrument;

comparing the amount of microorganisms recovered from each respective site in the decontaminated test instrument with the amount of microorganisms recovered from each respective site in the contaminated control instrument, and ascertaining the efficacy of the decontamination procedure employed.

26. A method according to claim 25, wherein the decontamination procedure is deemed effective relative to the sampling technique when the amount of microorganisms recovered from each site of the decontaminated test instrument is at least 3 logs less than the amount of microorganisms recovered from each site of the contaminated control instrument.

27. A method according to claim 26, wherein said surgical instrument is an endoscope.

28. A method according to claim 25, wherein the first sampling technique and the second sampling technique are one of direct microbiologic sampling techniques and indirect microbiologic sampling techniques.

29. A method according to claim 28, wherein the direct microbiologic sampling techniques include one of swabbing and brushing and the indirect microbiologic sampling techniques include one of flushing or rinsing with a sterile fluid.

30. A method according to claim 25, further comprising the step of determining the number of microorganisms recovered from the test and control instruments.

31. A method according to claim 28, further comprising the step of comparing the number of microorganisms recovered from the sites of the control instrument to the number of microorganisms applied initially to these sites and to determine efficacy of the first and second sampling techniques.

32. A method according to claim 25, wherein said instruments are reusable surgical instruments.

33. A method according to claim 25, wherein the first and second known amounts of inoculum comprise at least $1 \times 10^8$ colony forming units.

34. A method according to claim 33, wherein the step of recovering the microorganisms from the contaminated control instrument is at least $1 \times 10^6$ colony forming units.

35. A method according to claim 34, further comprising the step of permitting the inoculum to dry before performing the decontamination step.

* * * * *

UNITED STATES PATENT AND TRADEMARK OFFICE
CERTIFICATE OF CORRECTION

PATENT NO. : 6,428,746 B1
DATED : August 2, 2002
INVENTOR(S) : Lawrence F. Muscarella and Frank E. J. Weber It is certified that error appears in the above-identified patent and that said Letters Patent is hereby corrected as shown below:

Column 1,
Line 4, insert -- Related Application: This application is a continuation-in-part of application Serial No. 08/932,495, filed September 18, 1997, now abandoned, and claims priority therefrom. --.

Signed and Sealed this

Eighth Day of February, 2005

JON W. DUDAS
*Director of the United States Patent and Trademark Office*